(12) United States Patent
Gaind et al.

(10) Patent No.: US 10,067,072 B2
(45) Date of Patent: Sep. 4, 2018

(54) METHODS AND APPARATUS FOR SPECKLE SUPPRESSION IN LASER DARK-FIELD SYSTEMS

(71) Applicant: KLA-Tencor Corporation, Milpitas, CA (US)

(72) Inventors: Vaibhav Gaind, Fremont, CA (US); Jason C. Kirkwood, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 59 days.

(21) Appl. No.: 15/201,191

(22) Filed: Jul. 1, 2016

(65) Prior Publication Data

US 2017/0011495 A1 Jan. 12, 2017

Related U.S. Application Data

(60) Provisional application No. 62/190,729, filed on Jul. 10, 2015.

(51) Int. Cl.
| | |
|---|---|
| *G06K 9/00* | (2006.01) |
| *G01N 21/95* | (2006.01) |
| *H04N 5/225* | (2006.01) |
| *G01N 21/88* | (2006.01) |

(52) U.S. Cl.
CPC . *G01N 21/9501* (2013.01); *G01N 2021/8822* (2013.01); *H04N 5/2256* (2013.01)

(58) Field of Classification Search
None
See application file for complete search history.

(56) References Cited

U.S. PATENT DOCUMENTS

| | | | | |
|---|---|---|---|---|
| 5,699,447 | A | * 12/1997 | Alumot | G01N 21/94 348/126 |
| 2002/0131052 | A1 | * 9/2002 | Emery | G01N 21/95607 356/511 |
| 2004/0042001 | A1 | * 3/2004 | Vaez-Iravani | G01N 21/8806 356/237.2 |
| 2005/0141810 | A1 | 6/2005 | Vaez-Iravani et al. | |

(Continued)

OTHER PUBLICATIONS

Arlt, J., et al. "The production of multiringed Laguerre-Gaussian modes by computer-generated holograms." Journal of modern optics 45.6 (1998): 1231-1237. 8 pages.*

(Continued)

*Primary Examiner* — Ryan P Potts
(74) *Attorney, Agent, or Firm* — Kwan & Olynick, LLP

(57) ABSTRACT

A system for detecting defects on a semiconductor sample includes an illumination module for directing a nonzero-order Gaussian illumination beam towards a plurality of locations on a sample and a collection module for detecting light scattered from the sample in response to the nonzero-order Gaussian illumination beams and generating a plurality of output images or signals for each location on the sample. The system further comprises a processor system for detecting defects by (i) processing the output images or signals so as to retain filtered image or signal portions that substantially match a point spread function of the one or more nonzero-order Gaussian illumination beams, and (ii) analyzing the filtered image or signal portions to detect defects on the sample.

20 Claims, 7 Drawing Sheets

(56) References Cited

U.S. PATENT DOCUMENTS

| | | |
|---|---|---|
| 2006/0092515 A1 | 5/2006 | Kim et al. |
| 2006/0152810 A1 | 7/2006 | Kvamme |
| 2006/0229744 A1 | 10/2006 | Patzwald et al. |
| 2011/0075151 A1* | 3/2011 | Jeong .................. G01N 21/956 356/453 |
| 2012/0268812 A1* | 10/2012 | Anhut ................ G02B 21/0068 359/386 |
| 2013/0016346 A1* | 1/2013 | Romanovsky ..... G01N 21/9501 356/237.5 |
| 2015/0131893 A1 | 5/2015 | Sivaraman |

OTHER PUBLICATIONS

Bowen, John W. "Terahertz sensing and measuring systems." Advances in Spectroscopy for Lasers and Sensing. Springer, Dordrecht, 2006. 103-118. 16 pages.*

Cardano, Filippo, et al. "Generation and dynamics of optical beams with polarization singularities." Optics express 21.7 (2013): 8815-8820. 6 pages.*

"International Application Serial No. PCT/US2016/040991, Search Report dated Sep. 30, 2016", 3 pgs.

* cited by examiner

METHODS AND APPARATUS FOR SPECKLE SUPPRESSION IN LASER DARK-FIELD SYSTEMS

CROSS-REFERENCE TO RELATED APPLICATIONS

This application claims the benefit of prior application U.S. Provisional Application No. 62/190,729, filed 10 Jul. 2015 by Vaibhav Gaind et al., which application is incorporated herein by reference in its entirety for all purposes.

TECHNICAL FIELD OF THE INVENTION

The present invention relates generally to methods and systems for defect detection for semiconductor wafers or reticles in an inspection system and, more specifically, to reducing speckle effects during defect detection.

BACKGROUND

A diverse number and type of inspection systems are available for inspecting samples for defects. Lasers are often used as light sources in many inspection systems to detect defects on wafers or photomasks. Lasers provide one of the most efficient illumination methods due to their extremely high brightness.

One of the downsides, however, of using lasers is that the high spatial and temporal coherency of laser light can cause a ringing effect when imaging patterns on the surface of a sample, or speckle when the surface features are random (e.g., due to surface or line edge roughness). The ringing effect or speckle can severely degrade image quality and introduce excessive noise, therefore reducing sensitivity for detecting defects. Comprehensive discussions about interference effects such as ringing and speckle phenomena can be found in "Fourier Optics", by J. W. Goodman, McGraw-Hill, and "Statistical Optics", also by J. W. Goodman, Wiley-Interscience.

These deleterious image effects can be reduced in various manners. One conventional technique of providing partially incoherent laser light involves the use of a rotating diffuser. A rotating diffuser typically consists of a rotating ground-glass screen that is introduced into the path of the laser beam before it reaches the object being imaged. The rotating diffuser introduces random phase variations into the incident laser beam, thereby reducing the spatial coherence of the beam. As the diffuser rotates, a detector can collect images of the object from independent views or perspectives. The detector, in turn, can integrate the independent inspection views to effectively synthesize an incoherent illumination of the object being imaged. One problem associated with using a rotating diffuser involves illumination efficiency. Diffusers are generally low efficiency because of excessive scattering of light. Another issue associated with a rotating diffuser is that it acts as a vibration source which is not ideal for an illumination system. Finally, the rotation speed of the diffuser disk must be faster than the integration time of the detector to provide adequate speckle suppression. This is not possible for high throughput systems where the integration time of the detector can be as low as a few nanoseconds.

In view of the foregoing, improved metrology apparatus and techniques for defect detection, while reducing speckle effects, are needed.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a system for detecting defects on a semiconductor sample is disclosed. The system includes an illumination module for directing a nonzero-order Gaussian illumination beam towards a plurality of locations on a sample and a collection module for detecting light scattered from the sample in response to the nonzero-order Gaussian illumination beams and generating a plurality of output images or signals for each location on the sample. The system further comprises a processor system for detecting defects by (i) processing the output images or signals so as to retain filtered image or signal portions that substantially match a point spread function of the one or more nonzero-order Gaussian illumination beams, and (ii) analyzing the filtered image or signal portions to detect defects on the sample.

In a specific implementation, the illumination module comprises (i) a light source for generating the zero-order Gaussian illumination beam, (ii) a nonzero-order Gaussian generator for altering the zero-order Gaussian illumination beam to produce a nonzero-order Gaussian illumination beams, and (iii) one or more optical elements for directing the non-zero Gaussian illumination beams towards the sample. In a further aspect, the zero-order Gaussian illumination beam is a zero-order Laguerre Gaussian illumination beam and the nonzero-order Gaussian illumination beam is a nonzero-order Laguerre Gaussian illumination beam. In yet other aspects, the nonzero-order Gaussian generator is a spiral phase plate, a diffraction grating or hologram, or a spatial light modulator or q-plate.

In another embodiment, the collection module includes one or more detectors that are positioned to collect scattered light from the sample in response to the nonzero-order Gaussian illumination beam. In a further aspect, the filtered output images are Obtained by convolving a kernel image that matches the point spread function of the nonzero-order Gaussian illumination beam with the output images. In another aspect, the filtered output images are obtained by classifying the output images using a classifier that has been trained to define, as defects, images that match the point spread function of the nonzero-order Gaussian illumination beam. In another example embodiment, the collection module is arranged to collect the scattered light in a darkfield mode.

In an alternative embodiment the invention pertains to a method of detecting defects on a semiconductor sample. A plurality of positions of the sample are illuminated with a nonzero-order Gaussian illumination beam. Output images or signals are obtained from one or more detectors arranged to detect scattered light from the sample in response to the nonzero-order Gaussian illumination beam. The output images or signals are filtered so as to retain filtered image or signal portions that substantially match a point spread function of the nonzero-order Gaussian illumination beam. The filtered images or signals are analyzed to detect defects on the sample.

In a specific method implementation, illuminating a plurality of positions of the sample with a nonzero-order Gaussian illumination beam comprises (i) generating a zero-order Gaussian illumination beam, (ii) producing a nonzero-order Gaussian illumination beam from the zero-order Gaussian beam, and (iii) directing the nonzero-order Gaussian illumination beam towards the plurality of positions on the sample.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction

Traditional laser systems for inspecting semiconductor samples tend to utilize zero-order Gaussian beams so as to make the beam profile as tight as possible for facilitating inspection of very small structures. With the use of such coherent systems in dark field applications, the scattering effects of detects is almost identical to the scattering effect of surface or line roughness, which is referred to as the "speckle effect." Accordingly, it is difficult to distinguish defects from surface or line roughness. For instance, the intensity of defect may not be higher than the intensity of the speckle noise so that thresholding techniques for defining defects fails.

Various methods can be used to suppress speckle, such as channel fusion, which uses de-correlation between the collection channels to improve signal to noise ratio, cross-polarization in collection with respect to the illumination polarization, and the creation of partially coherent systems with angular or wavelength diversity. Also, matched filtering can be used to suppress uncorrelated noise sources like shot-noise. However, when a rough area is scanned with a zero-order Gaussian beam, the speckle that is generated retains the point spread function of the incident beam and, therefore, using a matched filter does not result in any improvement in the defect signal to noise ratio.

Figure 1A:
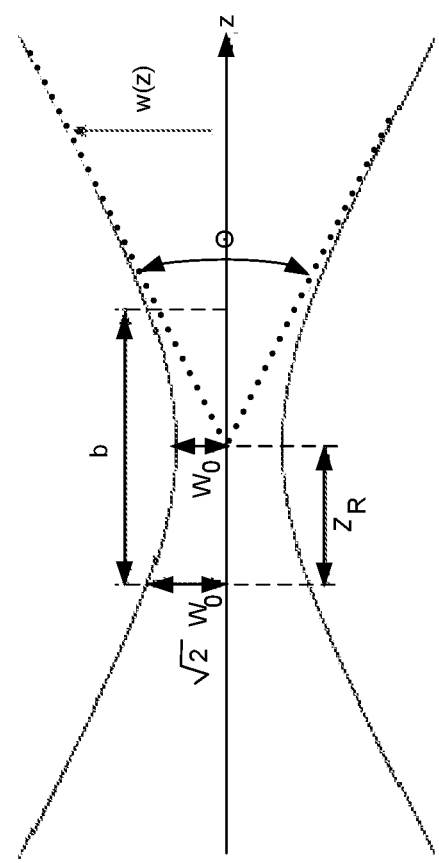
FIG. 1A illustrates Gaussian beam width as a function of the distance z along the beam.

Example Embodiments for Detecting Defects:

Certain embodiments of the present invention utilize a nonzero-order Gaussian beam to image the sample. A simple Gaussian beam will first be described. FIG. 1A illustrates Gaussian beam width as a function of the distance z along the beam. The diagram shows the following parameters: $w_0$ is the beam waist; b is the depth of focus; $z_R$ is the Raleigh range; and $\ominus$ is the total angular spread. The shape of a Gaussian beam of a given wavelength $\lambda$ is governed solely by the beam waist $w_0$, which is a measure of the beam size at the point of its focus (z=0) where the beam width w(z) is the smallest (and likewise where the intensity on-axis (r=0) is the largest). From this parameter the other parameters describing the Gaussian beam can be determined. For instance, $Z_R$ can be defined by:

$$z_R = \frac{\pi w_0^2}{\lambda}$$

Although the tails of a Gaussian function never actually reach zero, the "edge" of a beam is referred to as the radius, where r=w(z) increases linearly with z. That is where the intensity has dropped to 1/e2 of its on-axis value. That is, for $z \gg z_R$ the parameter w(z) increases linearly with z. This relationship means that far from the waist, the beam "edge" (in the above sense) is cone-shaped. The angle between lines along that cone (whose r=w(z)) and the central axis of the beam (r=0) is called the divergence of the beam, which is given by:

$$\theta \approx \frac{\lambda}{\pi w_0}$$

The total angular spread of the beam far from the waist is then given by:

$$\ominus = 2\theta$$

One type of nonzero-order Gaussian beam can take the form of a Laguerre-Gaussian (LG). Although certain embodiments are described herein as using a nonzero-order LG beam, other types of nonzero-order Gaussian beams (e.g., Hermite-Gaussian, Ince-Gaussian, Hypergeometric-Gaussian, flat-top, Bessel, Airy or fractal beams, etc.) may be used. The equation for an LG beam is given by:

$$u_{pl}(r, \phi, z) = \frac{C}{(1 + z^2/z_R^2)^2} \left[\frac{r\sqrt{2}}{w(z)}\right]^l L_p^l \left[\frac{2r^2}{w^2(z)}\right]$$

-continued $$\exp\left[\frac{-r^2}{w^2(z)}\right]\exp\frac{-ikr^2z}{2(z^2-z_R^2)}\exp(-il\phi)\exp\left[i(2p+l+1)\tan^{-1}\frac{z}{z_R}\right]$$

where C is a normalization constant; z is the axial distance from the beam's focus or waist; $k=2\pi/\lambda$ is the wave number (in radians per meter) for a wavelength $\lambda$; r is the radial distance from the center axis of the beam; $z_R$ is the Raleigh distance or range; p corresponds to the radial component of the beam; l is related to the azimuthal axis; $L_p^l$ are generalized Laguerre polynomials; w(z) is the radius at which the field amplitudes fall to 1/e of their axial values at the plane z along the beam; i is the imaginary unit. $Z_R$ is also defined as:

$$z_R = \frac{\pi w_0^2}{\lambda}$$

LG beams with l>0 carry an orbital angular momentum. The traditional Gaussian beam corresponds to l=0 and p=0 and results in a phase that is azimuthally symmetric. However, for l>0, the phase gets an additional contribution from $\exp(-il\phi)$. The effect of the rotational mode number l, in addition to affecting the Laguerre polynomial, is mainly contained in the phase factor $\exp(-il\phi)$, in which the beam profile is advanced (or retarded) by l complete $2\pi$ phases in one rotation around the beam (in $\varphi$).

LG beams can be generated using spiral phase plates or diffractive optical elements. Such phase plates for DUV and UV wavelengths can be obtained. Although the following examples illustrate generation of a nonzero-order illumination beam for which l is not zero, the p parameter may also be varied so as to form dipoles, quadrupoles, etc., depending on the particular inspection application.

Figure 1B:
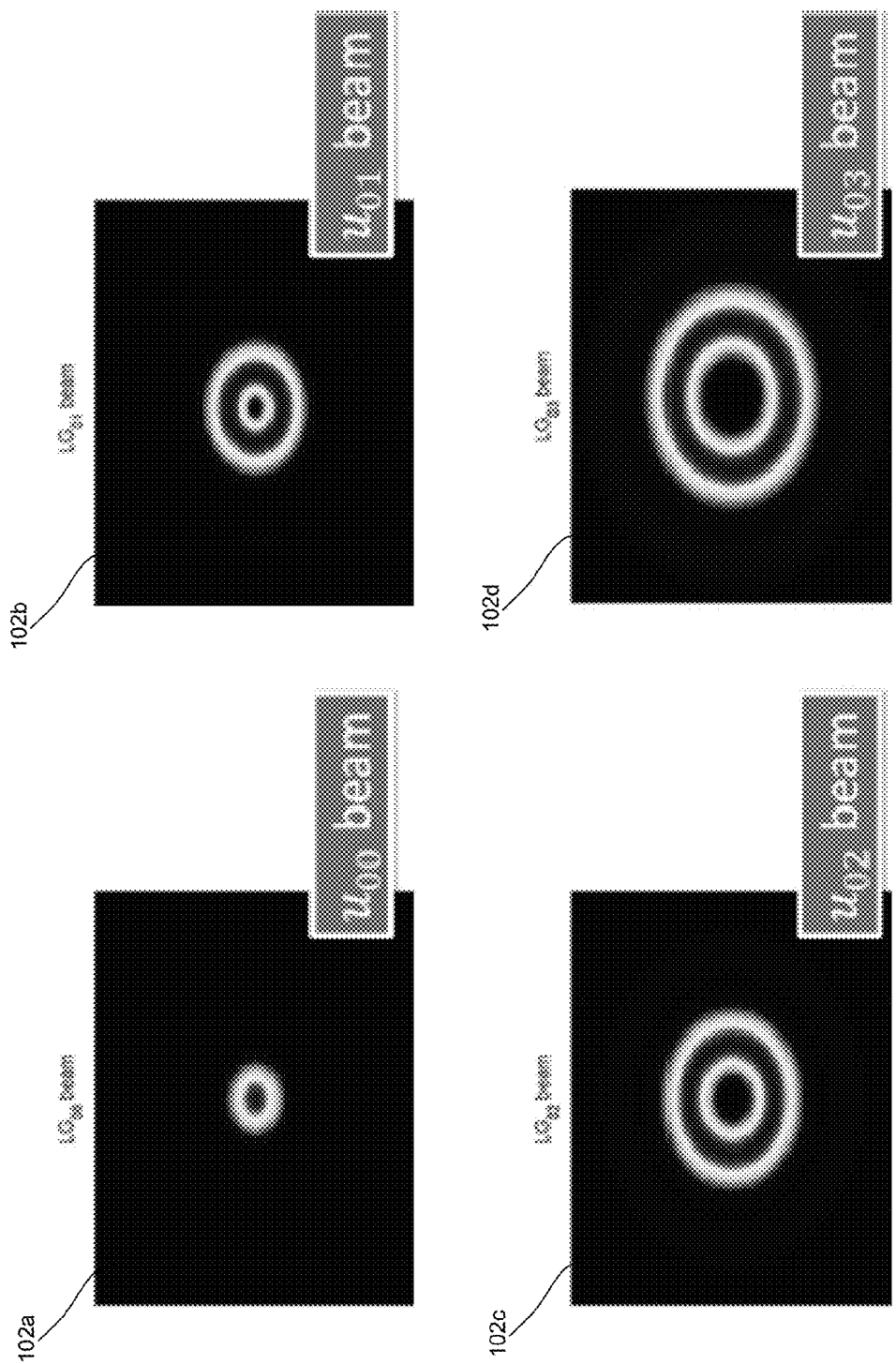
FIG. 1B illustrates several examples of Laguerre-Gaussian (LG) beam cross-sections.

FIG. 1B illustrates several example LG beams. As shown, different point spread functions (PSF's) of LG beams for different combinations of p=0, l=0, 1, 2, 3 are shown. PSF 102a corresponds to an $LG_{00}$ beam; PSF 102b corresponds to an $LG_{01}$ beam; PSF 102c corresponds to an $LG_{02}$ beam; and PSF 102d corresponds to an $LG_{03}$ beam.

In general, these LG beams all have toroid shaped rings of light on the sample. When a sample is illuminated by a toroid shaped beam profile, the scattering behavior of defects differs from the scattering behavior of surface roughness or line edge roughness. The scattering effect from the defect captures the shape of the illumination so that the defects result in a fully developed toroid shape. In contrast, the speckle scattering does not have a toroid or ring shape or merely has a partial ring shape. Said in another way, defect scattering is an energy transfer phenomenon, while surface roughness or line edge roughness is an interference phenomenon. For any nonzero-order Gaussian beam, it is likely that defect signal shape will be highly correlated with the incident beam point spread function (PST) shape.

Figure 2:
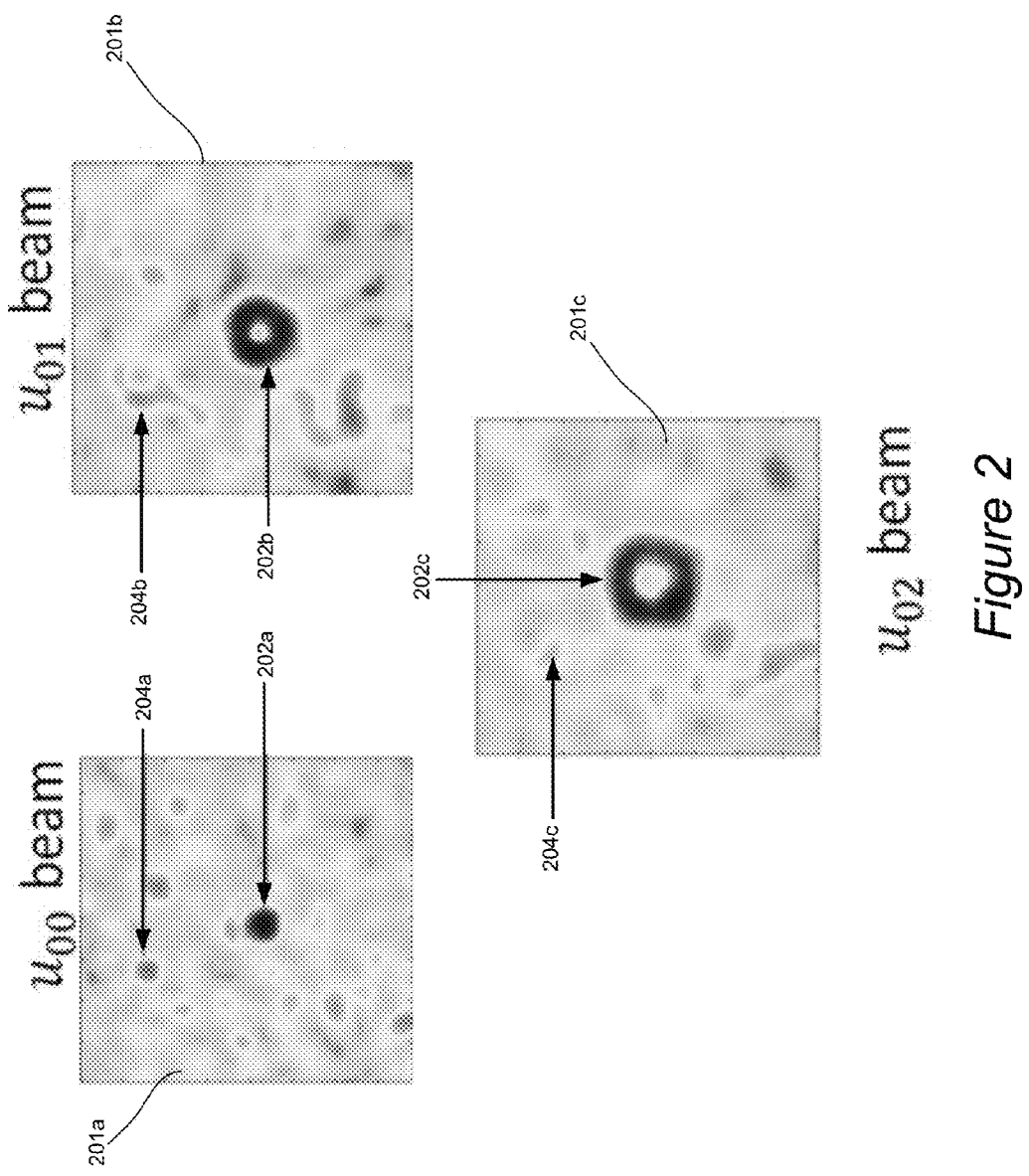
FIG. 2 illustrates the scattering (or dark field) defect images obtained by illuminating a defect and line edge roughness with different LG beams in accordance with one implementation of the present invention.

FIG. 2 illustrates the scattering (or dark field) defect images obtained by illuminating a defect and line edge roughness with different LG beams in accordance with one implementation of the present invention. In this example, the defect is a line protrusion in the presence of line edge roughness. As shown, defect image 201a results from illuminating a line edge roughness portion and defect on the sample with an $LG_{00}$ beam. Such defect image 201a contains a speckle image portion 204a from the line edge roughness portion and a defect image portion 202a from the defect.

As can be seen, the speckle image portion 204a has a similar intensity as the defect portion 202.a so that distinguishing the speckle from the defect may prove difficult.

For progressively higher ordered LG beams, however, the defect portion is enlarged and the speckle portion is diminished. For instance, increasing l results in an increase in the toroid size of the illumination beam. Defect image 201b contains speckle portion 204b and defect portion 202b for an $LG_{01}$ beam, and defect image 201c contains speckle portion 204c and defect portion 202c for an $LG_{02}$ beam. The defect image portion clearly retains the PSF of the higher order beam it was scanned with. That is, the defect image portion is matched to the PSF, while speckle spot image portions partially or do not match at all to the PSF of the corresponding higher order illumination beam.

Since speckle originates from interference of scattered waves, the likelihood that speckle will have constructive interference on all points of the PSF is low. That is, a speckle feature will likely have a different shape than the PST. An algorithmic or other type of filter can then be used on the collected image to recapture the energy effects of the defects, while minimizing the capturing of speckle noise. Accordingly, certain embodiments can implement filtering processes that filter the output images or signals that match the PSF of the nonzero-order Gaussian beams so as to readily locate the defects and not the speckle in a scattering image produced from a higher order LG beam. This filtering, which is based on the illumination beam's PSF, allows defects to be readily distinguished from speckle as further described herein.

Figure 3:
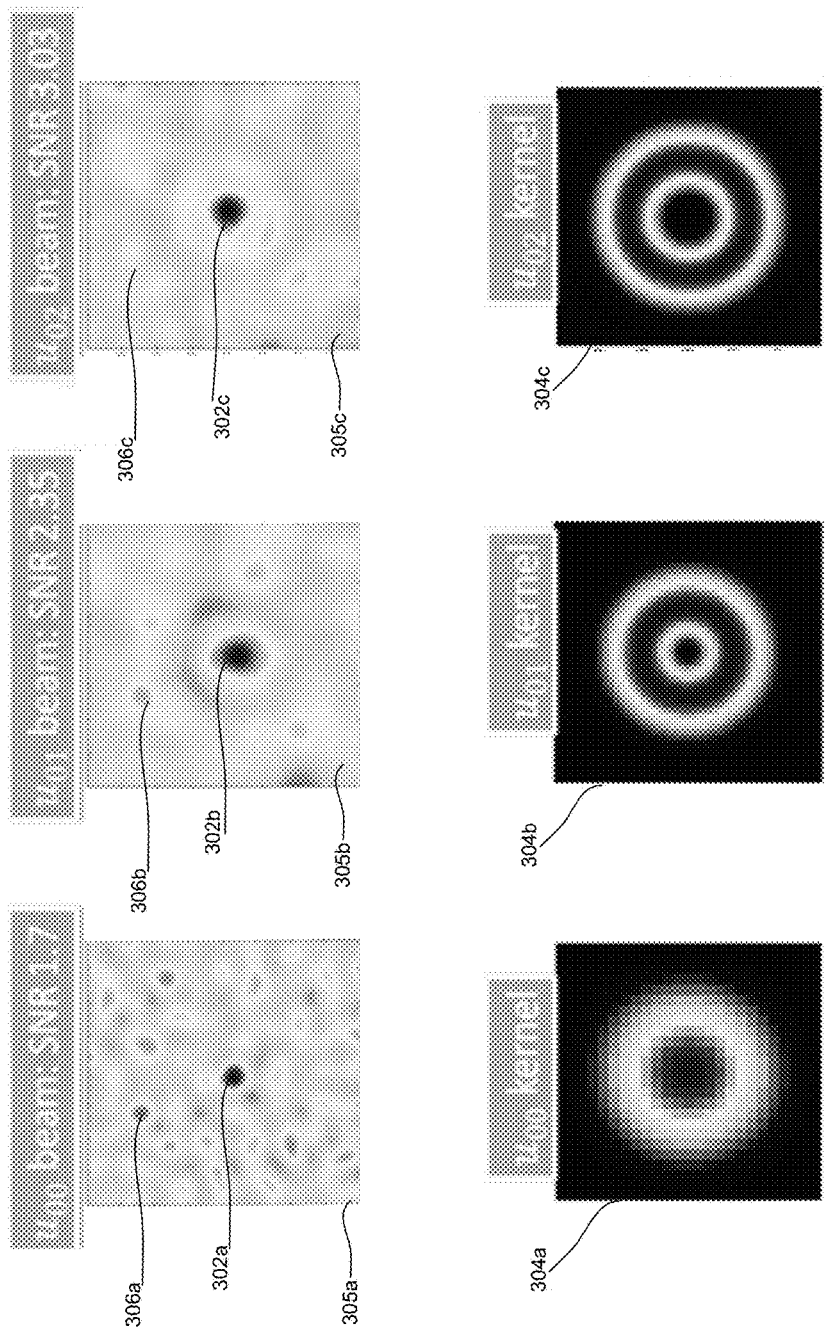
FIG. 3 illustrates filtered defect images that result from applying kernels that match the point spread function (PSF) of the illumination beam to the collected detect images in accordance with a specific implementation of the present invention.

FIG. 3 illustrates filtered detect images that result from applying kernels that match the illumination beam to the collected defect images in accordance with a specific implementation of the present invention. As shown, kernel 304a corresponding to a $\mu_{00}$ beam is applied to the scattering defect and speckle image produced by such LG beam, and results in filtered image 305a. This filtered image 305a contains speckle portion 306a and defect portion 302a. In contrast, kernel 304b corresponding to $\mu_{01}$ beam is applied to the detected image, resulting in filtered image 305b having speckle portion 306b and defect portion 302b. Lastly, kernel 304c corresponding to $\mu_{02}$ beam is applied to the detected image, resulting in filtered image 305c having speckle portion 306c and defect portion 302c. Even partial ring effects for the speckle are reduced and even disappear at increasingly higher orders. Thus, the presence of a partial ring (or absence of a ring entirely) reduces the magnitude of the speckle signal since such speckle images do not match the toroid rings of the kernel. The resulting filtered defects represent a significant boost in SNR (signal to noise ratio). An SNR of 1.8× is observed with the $\mu_{02}$ beam as compared to $\mu_{00}$ beam.

Figure 4:
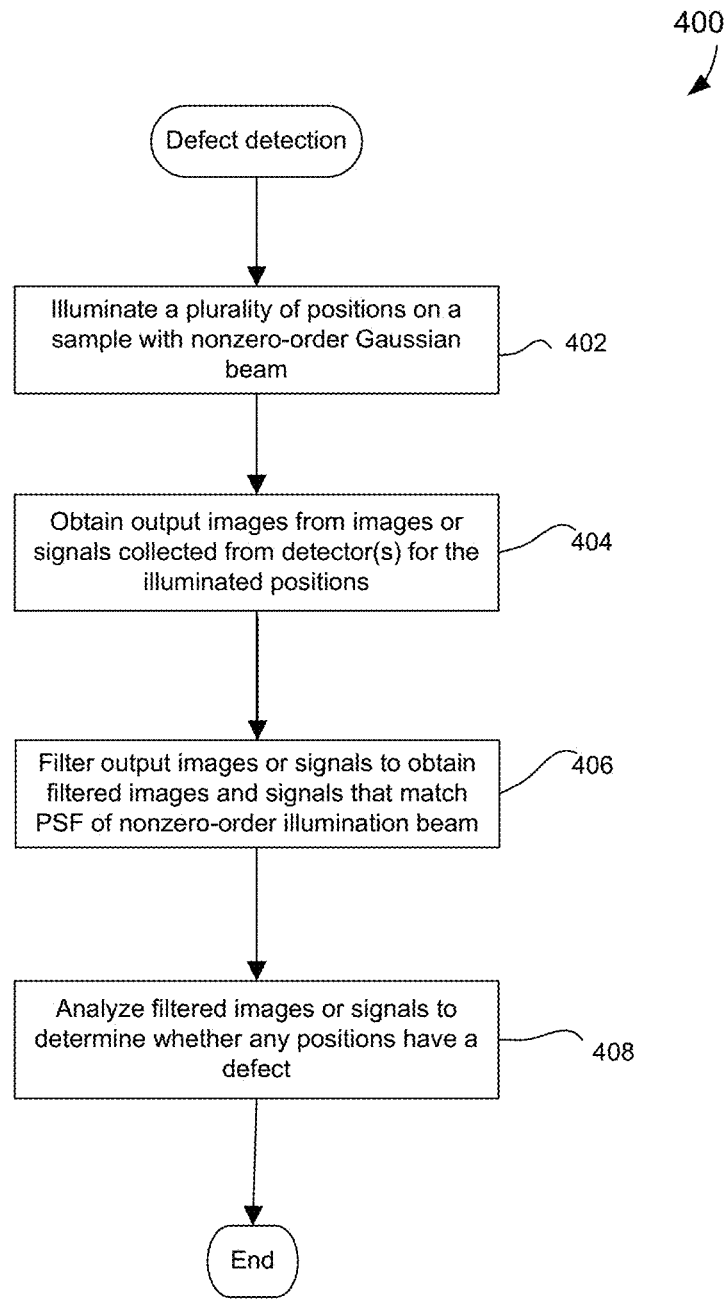
FIG. 4 is a flow chart illustrating a procedure for detecting defects using nonzero-order Gaussian beams and PSF-matched filtering in accordance with one embodiment of the present invention.

FIG. 4 is a flow chart illustrating a procedure 400 for detecting defects using nonzero-order Gaussian beams and PSF-matched filtering in accordance with one embodiment of the present invention. Although the illustrated procedure is described as being applied to darkfield defect inspection for semiconductor specimens, these techniques (and systems) are applicable for any type of defect detection that uses coherent illumination in which speckle is an issue.

Initially, a plurality of positions on a sample may be illuminated with a nonzero-order Gaussian beam in operation 402. For example, a zero-order Gaussian beam may be generated and passed through an optical element for altering the orbital angular momentum (OAM) of such beam to produce a nonzero-order Gaussian beam that is then scanned over the sample.

For example, a wafer (or other sample type) may be scanned relative to the illumination beam to obtain images for entire swath portions of the wafer. In order to obtain a signal or image from each location, the wafer may be moved relative to the beam column; the beam column may be moved relative to the wafer; or the beam column and wafer may both be moved relative to each other. The resulting image swaths may be broken into image patches that are individually analyzed in parallel or serially. Although all the patches of a wafer would be typically inspected with a single selected wavelength, an alternative approach may include inspecting each patch or set of patches with a selected wavelength setting, which is dependent on the particular material characteristics of such patch. Polarization and aperture setting may also be applied to the collected light.

Output images or signals may then be obtained from the images or signals that were collected from one or more detector(s) in operation 404. The output images may be formed in any suitable manner for analyzing defects. By way of examples, a die-to-die, cell-to-cell, or die-to-database technique may be used to obtain difference images by comparing test and reference images. For instance; output images may be obtained by subtracting an imaged test area that may differ from another reference image area, which is free of defects and obtained from another die, cell, or simulated from a design database.

The output images or signals are then filtered to obtain filtered images and signals that match the PSF of the non-zero illumination beam in operation 406. For instance, the images or signals may then be filtered based on a matching PSF kernel. That is, a filter that matches the PSF of the nonzero-order Gaussian beam may be used to filter detects from the detected images. For instance, if a $\mu_{02}$ incident beam is scanned across the sample, each resulting image may be filtered using a kernel that mimics the PSF for such $\mu_{02}$ incident beam (e.g., 304c). The PSF kernel can then be convolved with the output image to filter defects from such output image Other techniques may be used for filtering the defect images or signals. For instance, a classifier model (any machine-learning algorithms, such as neural networks, support-vector machines (SVM) or decision trees; or neural network) may be trained to filter out toroid shapes as defects.

The filtering process may be performed on either the detected images or the "difference" images that were obtained after comparison of test and references images. The result is the same. However, filtering the difference images may save computation time, as compared with filtering the images obtained from the detectors prior to comparing reference and test images.

The filtered images or signals may then be analyzed to determine whether the any positions have a defect in operation 408. The filtered signals or images may be analyzed in any suitable manner using any suitable technique. A defect may be flagged when a difference between a test and reference image area is more than a predefined threshold value, which may vary based on desired sensitivity levels for different pattern types or locations on the sample.

In one embodiment, the design database (that was used to fabricate the reticles and wafer under test) used to create reference optical images of the areas that are being imaged. In general, these reference images are rendered by simulating the reticle fabrication process and photolithography process to simulate wafer patterns. The inspection tool's physical configuration and optical characteristics (e.g., wavelength range, illumination and optical lens configurations, aberration effects, etc.) are also simulated to generate simulated wafer pattern images. In another embodiment, actual identical areas of an identical die or cell may be imaged with the inspection tool and used as reference areas to be compared to the test areas of a corresponding identical die or cell.

Defects on a sample may be repaired, or the sample may be discarded. A process for fabricating a next sample may be adjusted to minimize defects if the source of such defect can be determined. For instance, certain defect signatures may be associated with certain process conditions or issues during wafer fabrication, and such conditions or issues may be adjusted or corrected when such defect signatures are found on a wafer.

Certain embodiments of the present invention utilize mechanisms for adding information to the defect images without adding or minimally adding only part of such information to the nuisances, such as surface or line edge roughness. That is, structure is uniquely added to the detected defect image and not to the speckle images. The defect images contain unique morphological information that visually distinguishes them from the speckle images, which are not visually altered in the same way. This additional information for the defect images can then be used to filter such defect images from the nuisance images.

Overall, these mechanisms for using a nonzero-order Gaussian illumination beam with post-processing can be useful in dark-field imaging system, especially for large arrays, dep-layers, and back-end layers where the large wafer noise limits the use of dark-field systems. This could potentially significantly boost the sensitivity of dark-field systems on such wafers.

In general, an applicable inspection tool for implementation of techniques of the present invention may include at least one light source for generating a nonzero-order Gaussian incident light beam. Such an inspection may also include illumination optics for directing the incident beam to the area-of-interest, collection optics for directing an output beam that is emitted from the area-of-interest in response to the incident beam, a sensor for detecting an output beam and generating an image or signal from the detected output beam, and a controller for controlling the components of the inspection tool and facilitating defect detection, including post-collection filtering, as described further herein.

Figure 5:
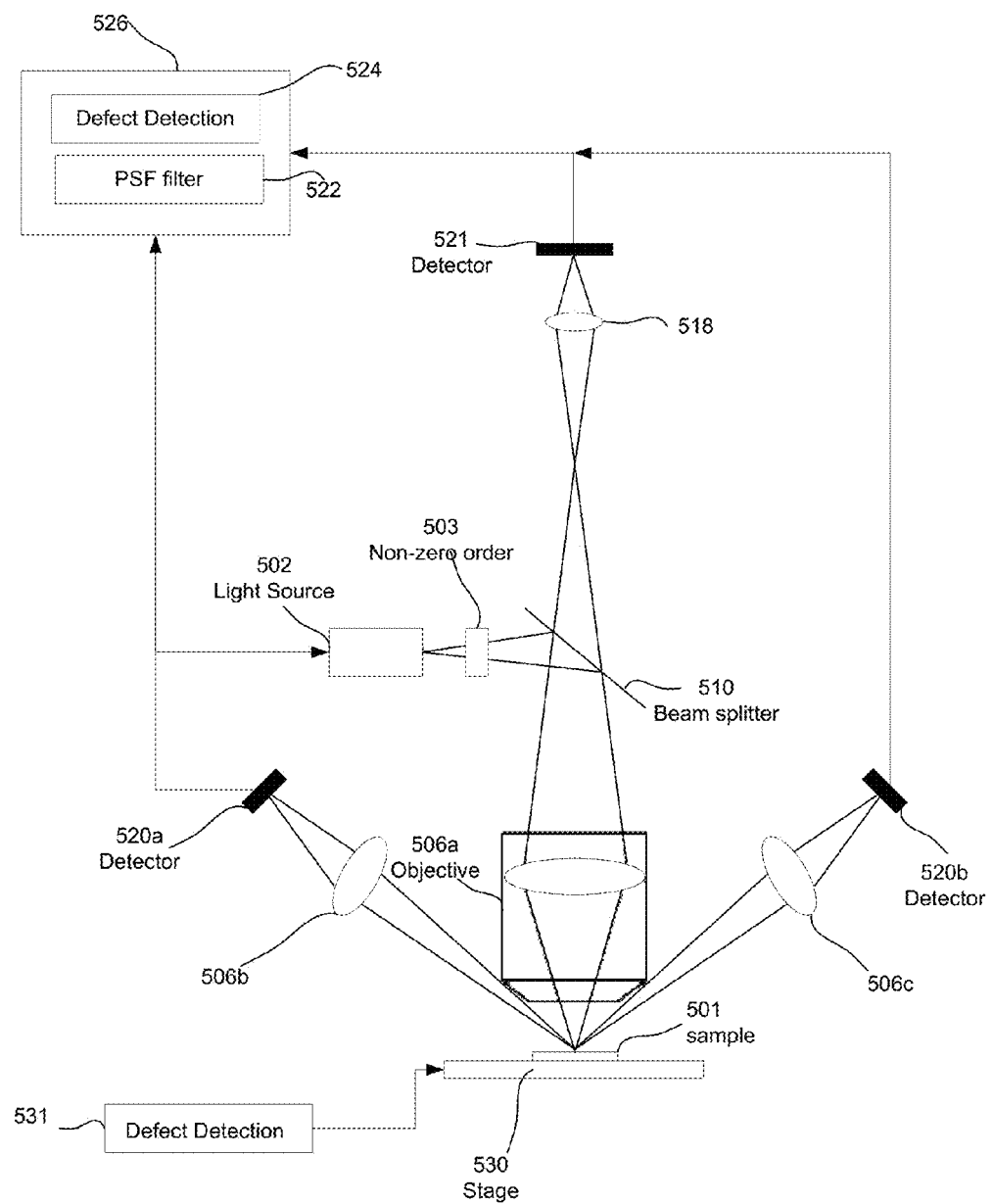
FIG. 5 is a diagrammatic representation of an inspection system with nonzero-order Gaussian illumination and PSF matching filtering in accordance with a specific implementation of the present invention.

FIG. 5 is a diagrammatic representation of an inspection system with nonzero-order Gaussian illumination and PSF matching filtering in accordance with a specific implementation of the present invention. As shown, the system 500 includes a light source 502 for generating a substantially coherent illumination beam. The output of the light source may take any suitable form, such as a laser source for generating a zero-order Gaussian beam. The illumination beam that is generated by the laser source is passed through nonzero-order generator 503 that alters the zero-order Gaussian beam to produce a nonzero-order Gaussian beam.

The nonzero-order generator 503 may take any suitable form for producing a nonzero-order Gaussian illumination beam. In one embodiment, a phase plate is inserted into the path of the incident beam. In effect, the nonzero-order generator 503 introduces an orbital angular momentum (OAM) for a nonzero-order. Orbital angular momentum of a given l state can be created by spiral phase plates, diffraction gratings/holograms, spatial light modulators, q-plates, etc.

Figure 6A:
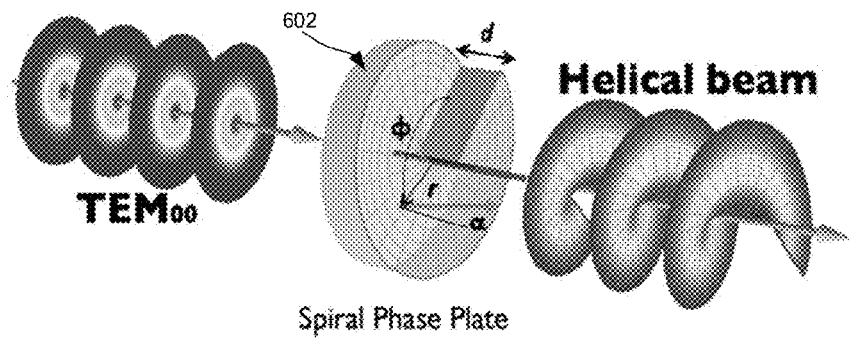
FIG. 6A illustrates a spiral wave plate for generating a helical beam from a standard traverse electromagnetic wave ($TEM_{00}$) in accordance with a specific implementation of the present invention.

Spiral wave plates, made of plastic or glass, are plates in which the thickness of the material increases in a spiral pattern in order to imprint a phase gradient on light passing through it. FIG. 6A illustrates a spiral wave plate 602 for generating a helical beam from a standard traverse electromagnetic wave ($TEM_{00}$) in accordance with a specific implementation of the present invention. For a given wavelength, an OAM state of a given l requires that the step height, the height between the thinnest and thickest parts of the plate, be given by $d=1\lambda/(n-1)$, where n is an integer. Although the wave plates themselves are efficient, they may be relatively expensive and may not be adjustable to different wavelengths.

Figure 6B:
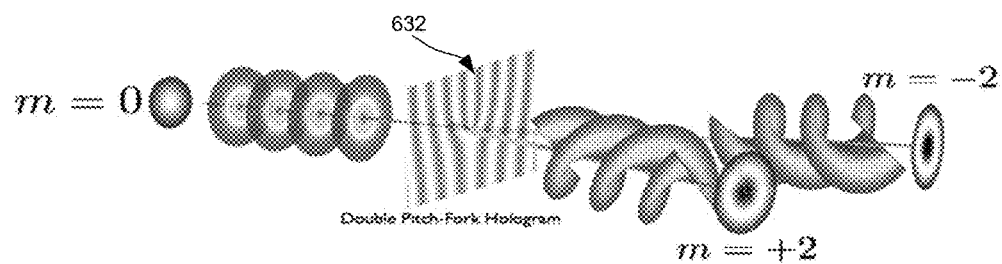
FIG. 6B illustrates use of a diffraction hologram with a fork dislocation for producing ±2 order Gaussian beams in accordance with another implementation of the present invention.

Another way to modify the phase of the light is with a diffraction grating or hologram. For an l=0 state, the diffraction grating/hologram would consist of parallel lines. However, for an l=1 state, there will be a "fork" dislocation, and the number of lines above the dislocation will be one larger than below. FIG. 6B illustrates use of a diffraction hologram with a fork dislocation (632) for producing a nonzero-order Gaussian beam in accordance with another implementation of the present invention. An OAM state with l>1 can be created by increasing the difference in the number of lines above and below the dislocation. As with the spiral wave plates, these diffraction gratings/holograms are fixed for l, but are not restricted to a particular wavelength. A spatial light modulator can be configured to work in the same way as the diffraction grating/hologram, but can be controlled by computer to dynamically generate a wide range of OAM states.

Figure 6C:
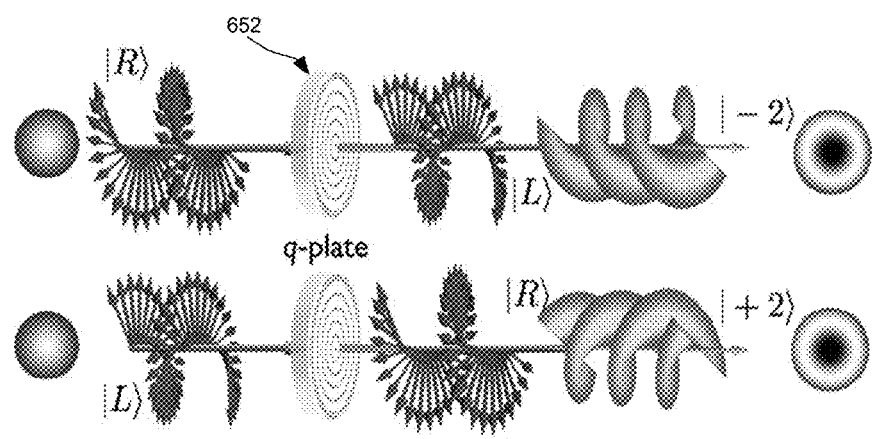
FIG. 6C illustrates use of q-plates for producing ±2 order Gaussian beams in accordance with another implementation of the present invention.

Another method for generating OAM is based on the light Spin Angular Momentum (SAM)-OAM coupling that may occur in a medium which is both anisotropic and inhomogeneous. In particular, a q-plate may be inserted into the incident beam path. A q-plate can be constructed using liquid crystals, polymers or sub-wavelength gratings, which can generate OAM by exploiting a SAM sign-change. In this case, the OAM sign is controlled by the input polarization. FIG. 6C illustrates use of q-plates (e.g., 652) for producing ±2 order Gaussian beams in accordance with another implementation of the present invention.

These features can be used in conjunction with other mechanisms for reducing speckle, such as rotating diffusers, channel fusion, cross polarization in the collection channels, creation of partially coherent systems via wavelength or angular variation, etc. Several speckle reduction techniques and apparatus are further described in U.S. Pat. No. 7,319,229, issued 15 Jan. 2008 by Mehdi Vaez-Iravani et al, which patent is incorporated herein by reference in its entirety for all purposes.

The light source may take any form for generating one or more electromagnetic waveforms, in addition to a coherent light source for generating, for example, a zero-order Gaussian laser beam. That is, multiple light sources may also be used. The one or more light sources may generate light having only one wavelength (e.g., monochromatic light), light having a number of discrete wavelengths (e.g., polychromatic light), light having multiple wavelengths (e.g., broadband light), and/or light that sweeps through wavelengths, either continuously or hopping between wavelengths (e.g., tunable sources or swept sources). For instance, different wavelengths may be used with different materials to achieve transparency or opaqueness with respect to the incident light on the material under test. A laser light source can be used for the light source 502, which can provide a higher brightness compared to spectroscopic methods, such as white light interferometry and chromatic confocal microscopy. Laser light sources, such as diode lasers, improve lifetime, stability, and thermal control of the light source. Other examples of suitable light sources are: a white light source, an ultraviolet (UV) laser, an arc lamp or an electrode-less lamp, colored or white light emitting diodes (LEDs), a laser sustained plasma (LSP) source, for example, those commercially available from Energetiq Technology, Inc. of Woburn, Mass., a supercontinuum source (such as a broadband laser source) such as those commercially available from NKT Photonics Inc. of Morganville, N.J., or shorter-wavelength sources such as x-ray sources, extreme UV sources, or some combination thereof. The light source(s) may also be configured to provide light having sufficient brightness, which in some cases may be a brightness greater than about 1 W/(nm cm2 Sr). The inspection system may also include a fast feedback to the light source for stabilizing its power and wavelength. Output of the light source can be delivered via free-space propagation, or in some cases delivered via optical fiber or light guide of any type.

The incident beam from the light source may generally pass through any number and type of lenses which serve to relay (e.g., shape, focus or adjust focus offset, filter/select wavelengths, filter/select polarization states, resize, magnify, reduce distortion, etc.) the beam towards a sample.

A polarization setting may also be applied to the longer or shorter wavelength range. For instance, a horizontal or vertical polarization may be selected for the selected wavelength range. A polarization setting may be applied based on any suitable inspection parameter, such as defect type, sample composition, wavelength range or sub-band selection, etc.

An aperture setting may also be inserted into the illumination (and collection) paths. For instance, an aperture setting for achieving a particular set of angles of incidence (AOI's) may be selected based any suitable inspection parameter, such as defect type, sample composition, type of sample structure being inspected, polarization setting, wavelength range or sub-band selection, etc.

The objective 506 may be a high magnification objective lens, such as a tele-centric type. Some or all of the incident light passes through the objective lens 506 onto at least a portion of the sample 501. The spot size of the incident light at the illumination point may be diffraction limited.

Certain inspection system embodiments can be configured for inspecting semiconductor samples, such as wafers and reticles. Other types of samples that may be inspected or imaged using the inspection apparatus of the present invention include solar panel structures, optical disks, etc.

The sample 501 may also be disposed on a stage 530 configured to position the sample 501 to receive the incident light at particular measurement sites. The sample 501 may be clamped to the stage in one instance, such as through mechanical and/or electrostatic clamping.

The stage 530 can be fixed or can scan in the x-direction, y-direction, and/or z-direction. For example, the stage can translate the sample 501 in a plane perpendicular to the axis of the incident light (e.g., the x-y plane) or a direction that is parallel to such incident axis (e.g., the z axis).

The inspection system 500 may also include a positioning mechanism 531 for moving the stage 530 (and sample 501) relative to the incident beam. By way of examples, one or more motor mechanisms may each be formed from a screw drive and stepper motor, linear drive with feedback position, or band actuator and stepper motor. The one or more positioning mechanisms 531 may also be configured to move other components of the inspection system, such as illumination or collection mirrors, apertures, wavelength filters, polarizers, etc.

Light is then reflected and scattered from the sample 501. The output beam may be directed and shaped by any suitable number and type of collection optics (e.g., 506*a*, 506*b*, 506*c*, 518), such as a pupil relay, one or more mirrors or lenses, a polarizer, aperture, and optics elements for zooming and focusing the output beam onto one or more detectors (e.g., 520*a*, 520*b*, 521). As shown, detectors 520*a* and 520*b* receive scattered darkfield light in two channels, while detector 521 is arranged to receive reflected output light. By way of example, the detectors may include a CCD (charge coupled device) or TDI (time delay integration) detector, photomultiplier tube (PMT), or other sensor.

The system 500 may also include a controller or computer system 526. For instance, the signals captured by each detector can be processed by controller 526, which may include a signal processing device having an analog-to-digital converter configured to convert analog signals from each sensor into digital signals for processing.

In a specific implementation, the controller 526 includes a PSF filter 522 for filtering the toroid shapes from the detected scattered darkfield images or signals and a defect detection module 524 for finding defects as described above. Although the inspection system is illustrated as having two darkfield channels, any suitable number of channels may be used to collect any portion or substantially all of the darkfield scattered light.

The controller may be configured to analyze intensity, phase, and/or other characteristics of the sensed light beam. The controller may be configured (e.g., with programming instructions) to provide a user interface (e.g., on a computer screen) for displaying resultant test images and other inspection characteristics as described further herein. The controller may also include one or more input devices (e.g., a keyboard, mouse, joystick) for providing user input, such as changing wavelength, polarization, or aperture configuration, viewing detection results data or images, setting up an inspection tool recipe.

Techniques of the present invention may be implemented in any suitable combination of hardware and/or software. The controller typically has one or more processors coupled to input/output ports, and one or more memories via appropriate buses or other communication mechanisms.

The controller may be any suitable combination of software and hardware and may be generally also configured to control various components of the inspection system. For instance, the controller may control selective activation of the illumination source, the illumination or output aperture settings, wavelength band, focus offset setting, polarization settings, etc. The controller may also be configured to receive the images or signals obtained from each detector and analyze the resulting images or signals to determine whether defects are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions; such as read-only memory devices (ROM) and random access memory (RAM). Examples of program instructions include both machine code, such as produced by a compiler, and files containing higher level code that may be executed by the computer using an interpreter.

It should be noted that the above description and drawings of an inspection system are not to be construed as a limitation on the specific components of the system and that the system may be embodied in many other forms. For example, it is contemplated that the inspection or measurement tool may have any suitable features from any number of known imaging or metrology tools arranged for detecting defects and/or resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may also be contemplated as forming part of the inspection or metrology apparatus.

Any suitable lens arrangement may be used to direct the incident beam towards the sample and direct the output beam emanating from the sample towards a detector. The illumination and collection optical elements of the system may be reflective or transmissive. The output beam may be reflected or scattered from the sample or transmitted through the sample. Likewise, any suitable detector type or number of detection elements may be used to receive the output beam and provide an image or a signal based on the characteristics (e.g., intensity) of the received output beam.

For future wafer defect inspection, a defect signal is significantly reduced due to DR shrink. Therefore, since there is a general trend for achieving higher defect signals with decreasing wavelength, it is desirable to have shorter wavelengths, better resolution, and smaller inspection pixels. However, such a shorter wavelength inspection configuration can have the disadvantages of small depth of focus, high thermal sensitivity to focus change, lower throughput, etc. Certain system embodiments provide features to track & correct focus, adjust system parameters to optimize S/N, etc. In addition, this arrangement allows more information to be obtained in one scan to make inspection cost-effective. Also, by acquiring multiple information at one single scan, post processing for defect characterization, signal enhancement, and noise/nuisance reduction can be effectively performed.

The inspection tool can comprise one or more hardware configurations which may be used in addition to certain embodiments of this invention as described above. Examples of such hardware configurations include, but are not limited to, the following: beam profile reflectometer (angle-resolved reflectometer), broadband reflective spectrometer (spectroscopic reflectometer), single-wavelength reflectometer, angle-resolved reflectometer, imaging system, and scatterometer (e.g. speckle analyzer)

The hardware configurations can be separated into discrete operational systems. On the other hand, one or more hardware configurations can be combined into a single tool. One example of such a combination of multiple hardware configurations into a single tool is further illustrated and described U.S. Pat. No. 7,933,026, which patent is herein incorporated by reference in its entirety for all purposes. The system may include certain lenses, collimators, mirrors, quarter-wave plates, polarizers, detectors, cameras, apertures, and/or light sources. The wavelengths for the optical systems can vary from about 120 nm to 3 microns. The signals collected can be polarization-resolved or unpolarized.

The system may include multiple metrology heads integrated on the same tool. However, in many cases, multiple metrology tools are used for measurements on a single area or multiple areas on the sample. Several embodiments of multiple tool metrology are further described, e.g., in U.S. Pat. No. 7,478,019 by Zangooie et al, entitled "Multiple tool and structure analysis", which patent is incorporated herein by reference in its entirety for all purposes.

It should be recognized that the various steps described throughout the present disclosure may be carried out by a single processor system or, alternatively, a multiple processor system. Moreover, different subsystems of the system, such as the above described light source and/or detector system embodiments, may include a computer system suitable for controlling system status, preprocessing signals, or carrying out at least a portion of the steps described herein. Therefore, the aforementioned description should not be interpreted as a limitation on the present invention but merely an illustration. Further, the one or more processor system may be configured to perform any other step(s) of any of the method embodiments described herein.

In addition, the processor system may be communicatively coupled to a detector system in any manner known in the art. For example, the one or more processor system may be coupled to computing systems associated with the detector system. In another example, the detector system may be controlled directly by a single computer system coupled to processor system.

The processor system may be configured to receive and/or acquire data or information (e.g., measurement signals, difference signals, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the processor system and other systems (e.g., external memory, reference measurement source, or other external systems). For example, processor system may be configured to receive measurement data from a storage medium (e.g., internal or external memory) via a data link. For instance, results obtained using the detection system may be stored in a permanent or semi-permanent memory device (e.g., internal or external memory). In this regard, the spectral results may be imported from on-board memory or from an external memory system. Moreover, the processor system may send data to other systems via a transmission medium. For instance, qualitative and/or quantitative results determined by processor system may be communicated and stored in an external memory. In this regard, measurement results may be exported to another system.

The processor system may include, but is not limited to, CPU, GPU board, FPGA, programmable logic arrays, a personal computer system, mainframe computer system, workstation, image computer, or any other device known in the art. In general, the term "processor system" may be broadly defined to encompass any device having one or more processors, which execute instructions from a memory medium. Program instructions implementing methods such as those described herein may be transmitted over a transmission medium such as a wire, cable, or wireless transmission link. Program instructions may be stored in a computer readable medium (e.g., memory). Exemplary computer-readable media include read-only memory, flash memory, a random access memory, or a magnetic or optical disk.

The inspection tool may be designed to make many different types of measurements related to semiconductor manufacturing. Additional metrology techniques for determining specific target characteristics may also be combined with the above-described defect detection techniques. For example, in certain embodiments the tool may also measure signals and determine other characteristics of one or more targets, such as quality and defect quantity values, critical dimensions, overlay, film thicknesses, process-related parameters (e.g., plating conditions), etc. The targets can include certain regions of interest, such as grating, Cu-pillars for interconnections between chips. Targets can include multiple layers (or films), such as photoresist or passivation layers.

Collected data can be analyzed by a number of data fitting and optimization techniques and technologies including machine-learning algorithms, such as neural networks, support-vector machines (SVM); dimensionality-reduction algorithms such as, e.g.; PCA (principal component analysis), ICA (independent component analysis), LLE (local-linear embedding); Kalman filter; algorithms to promote matching from same or different tool types, and others.

Computational algorithms are usually optimized for data process speed and accuracy with one or more approaches being used such as design and implementation of computational hardware, parallelization, etc. Different implementations of algorithms can be done in firmware, software, FPGA, programmable logic array, etc.

The data analysis may be used to pursue one of the following goals: measurement of height, quality, defect number, CD, composition, films, generating process parameters (e.g., plating or etching settings), and/or any combination thereof.

Certain embodiments of the present invention presented here generally address the field of semiconductor process and quality control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A system for detecting defects on a semiconductor sample, comprising:
   an illumination optics module for directing a nonzero-order Gaussian illumination beam towards a plurality of locations on a sample;
   a collection optics module for detecting light scattered from the sample in response to the nonzero-order Gaussian illumination beam and generating a plurality of output images or signals for the plurality of locations on the sample; and
   a processor system for detecting defects by:
      processing the output images or signals so as to retain filtered image or signal portions that match toroidal rings of a point spread function of the nonzero-order Gaussian illumination beam, wherein image or signal portions for defects tend to match the toroidal rings while image or signal portions for speckle noise do not tend to match the toroidal rings, and analyzing the filtered image or signal portions to detect defects on the sample.

2. The system of claim 1, wherein the illumination optics module comprises:
   a light source for generating a zero-order Gaussian illumination beam;
   nonzero-order Gaussian optics for altering the zero-order Gaussian illumination beam to produce a nonzero-order Gaussian illumination beams; and
   one or more optical elements for directing the non-zero Gaussian illumination beam towards the sample.

3. The system of claim 2, wherein the zero-order Gaussian illumination beam is a zero-order Laguerre Gaussian illumination beam and the nonzero-order Gaussian illumination beam is a nonzero-order Laguerre Gaussian illumination beam.

4. The system of claim 2, wherein the nonzero-order Gaussian optics is a spiral phase plate.

5. The system of claim 2, wherein the nonzero-order Gaussian optics is a diffraction grating or hologram.

6. The system of claim 2, wherein the nonzero-order Gaussian optics is a spatial light modulator or q-plate.

7. The system of claim 2, wherein the collection optics module includes one or more detectors that are positioned to collect scattered light from the sample in response to the nonzero-order Gaussian illumination beam.

8. The system of claim 7, wherein the filtered output image portions are obtained by convolving a kernel image that matches the point spread function of the nonzero-order Gaussian illumination beam with the output images.

9. The system of claim 7, wherein the filtered output image portions are obtained by classifying the output images using a classifier that has been trained to define, as defects, images that match the point spread function of the nonzero-order Gaussian illumination beam.

10. The system of claim 1, wherein the collection optics module is arranged to collect the scattered light in a darkfield mode.

11. A method of detecting defects on a semiconductor sample, comprising:
    illuminating a plurality of positions of the sample with a nonzero-order Gaussian illumination beam;
    obtaining output images or signals from one or more detectors arranged to detect scattered light from the sample in response to the nonzero-order Gaussian illumination beam;
    filtering the output images or signals so as to retain filtered image or signal portions that match toroidal rings of a point spread function of the nonzero-order Gaussian illumination beam, wherein image or signal portions for defects tend to match the toroidal rings while image or signal portions for speckle noise do not tend to match the toroidal rings; and
    analyzing the filtered images or signals to detect defects on the sample.

12. The method of claim 11, wherein illuminating a plurality of positions of the sample with a nonzero-order Gaussian illumination beam comprises:
    generating a zero-order Gaussian illumination beam;
    producing a nonzero-order Gaussian illumination beam from the zero-order Gaussian beam; and
    directing the nonzero-order Gaussian illumination beam towards the plurality of positions on the sample.

13. The method of claim 12, wherein the zero-order Gaussian illumination beam is a zero-order Laguerre Gaussian illumination beam and the nonzero-order Gaussian illumination beam is a nonzero-order Laguerre Gaussian illumination beam.

14. The method of claim 12, wherein the nonzero-order Gaussian illumination beam is produced by a spiral phase plate.

15. The method of claim 12, wherein the nonzero-order Gaussian illumination beam is produced by a diffraction grating or hologram.

16. The method of claim 12, wherein the nonzero-order Gaussian illumination beam is produced by a spatial light modulator or q-plate.

17. The method of claim 12, wherein the one or more detectors are positioned to collect scattered light from the sample in response to the nonzero-order Gaussian illumination beam.

18. The method of claim 17, wherein the filtered output image portions are obtained by convolving a kernel image that matches the point spread function of the nonzero-order Gaussian illumination beam with the output images.

19. The method of claim 17, wherein the filtered output image or signal portions are obtained by classifying the output images using a classifier that has been trained to define, as defects, images that match the point spread function of the nonzero-order Gaussian illumination beam.

20. The method of claim 11, wherein the output images or signals are obtained based on collection of scattered light in a darkfield mode.

* * * * *